(12) United States Patent
Berndt et al.

(10) Patent No.: US 7,176,335 B2
(45) Date of Patent: Feb. 13, 2007

(54) METHOD FOR PRODUCING METHACROLEIN FROM ISOBUTANE

(75) Inventors: Silke Berndt, Mannheim (DE); Klaus Joachim Mueller-Engel, Stutensee (DE); Goetz-Peter Schindler, Mannheim (DE); Frank Rosowski, Mannheim (DE); Jochen Petzoldt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/482,337

(22) PCT Filed: Jun. 28, 2002

(86) PCT No.: PCT/EP02/07174

§ 371 (c)(1),
(2), (4) Date: Dec. 29, 2003

(87) PCT Pub. No.: WO03/002492

PCT Pub. Date: Jan. 9, 2003

(65) Prior Publication Data

US 2004/0171887 A1    Sep. 2, 2004

(30) Foreign Application Priority Data

| Jun. 29, 2001 | (DE) | ................................. 101 31 297 |
| Mar. 13, 2002 | (DE) | ................................. 102 11 275 |
| May 2, 2002 | (DE) | ................................. 102 19 686 |

(51) Int. Cl.
*C07C 45/29* (2006.01)
*C07C 51/16* (2006.01)
*C07C 67/00* (2006.01)

(52) U.S. Cl. ...................... 568/476; 568/478; 568/479; 562/531; 562/532; 562/534; 560/210

(58) Field of Classification Search ................ 568/476, 568/478, 479; 562/531, 532, 534; 560/210
See application file for complete search history.

(56) References Cited

U.S. PATENT DOCUMENTS

| 4,234,519 A | * | 11/1980 | Yeoman et al. | .............. 568/492 |
| 4,413,147 A | * | 11/1983 | Khoobiar | .................... 568/476 |
| 4,520,125 A | * | 5/1985 | Baer et al. | .................. 502/170 |
| 5,166,119 A | * | 11/1992 | Oh-Kita et al. | ............. 502/205 |

FOREIGN PATENT DOCUMENTS

DE         33 13 573        10/1983

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process prepares methacrolein from isobutane by subjecting isobutane to a partial catalytic dehydrogenation in the gas phase and using the isobutenic product gas mixture to charge an oxidation zone in which the isobutene is oxidized to methacrolein in the gas phase with heterogeneous catalysis using molecular oxygen accompanied by molecular nitrogen as the oxygen source.

15 Claims, No Drawings

METHOD FOR PRODUCING METHACROLEIN FROM ISOBUTANE

The present invention relates to a process for preparing methacrolein from isobutane by A) subjecting the isobutane in a reaction zone A to a partial selective heterogeneously catalyzed dehydrogenation in the gas phase to form a product gas mixture A which comprises isobutene and unconverted isobutane, B) passing the isobutane and isobutene-containing product gas mixture A into a reaction zone B and subjecting the isobutene in the reaction zone B to a selective heterogeneously catalyzed partial oxidation in the gas phase using molecular oxygen to form a methacrolein-containing product gas mixture; B and C) using the methacrolein contained in the product gas mixture B either for preparing methacrylic acid or for another purpose and either recycling at least unconverted isobutane contained in the, product gas mixture B into reaction zone A or using it for another purpose.

Methacrolein is an important intermediate which finds use, for example, for preparing methacrylic acid. Methacrylic acid is an important staple chemical which is used as such and/or in the form of its methyl ester for preparing polymers which are used, for example, finely dispersed in an aqueous medium as a binder.

DE-A 3313573 discloses a process for preparing methacrolein from isobutane as described at the outset. On page 28, DE-A 3313573 recommends the use of virtually pure molecular oxygen as the source for the molecular oxygen required in reaction zone B. Although it would be possible to work with less pure molecular oxygen, preference is given to the use of pure molecular oxygen.

However, a disadvantage of such a use of substantially pure molecular oxygen as the oxygen source for reaction zone B is that isobutane accompanying the isobutene in reaction zone B does not then behave completely inertly, but is instead likewise partially and/or completely oxidized to a perceptible extent. While the latter in particular causes an undesired loss of isobutane, partial oxidation products of isobutane, for example isobutyraldehyde or isobutyric acid, are generally undesired companions of methacrolein and generally interfere in its subsequent uses and can only be removed from methacrolein with difficulty (even when they are only formed in small amounts).

It is an object of the present invention to provide a process for preparing methacrolein from isobutane as described at the outset which only has the above-described disadvantages to a reduced extent.

We have found that this object is achieved by a process for preparing methacrolein from isobutane by A) subjecting the isobutane in a reaction zone A to a partial selective heterogeneously catalyzed dehydrogenation in the gas phase to form a product gas mixture A which comprises isobutene and unconverted isobutane, B) passing the isobutane- and isobutene-containing product gas mixture A into a reaction zone B and subjecting the isobutene in the reaction zone B to a selective heterogeneously catalyzed partial oxidation in the gas phase using molecular oxygen to form a methacrolein-containing product gas mixture B and C) using the methacrolein contained in the product gas mixture B either for preparing methacrylic acid or for another purpose and either recycling at least unconverted isobutane contained in the product gas mixture B into reaction zone A or using it for another purpose, which comprises feeding the molecular oxygen required in reaction zone B to reaction zone B accompanied by molecular nitrogen in a molar ratio R of molecular oxygen to molecular nitrogen of from 1:1 to 1:10.

In other words, according to the invention, R may be 1:2, or 1:3, or 1:4, or 1:5, or 1:6, or 1:7, or 1:8, or 1:9, or 1:10. An advantageous ratio R is in the range from 1:2 to 1:8 or in the range from 1:3 to 1:8, or from 1:4 to 1:7. In the process according to the invention, the abovementioned accompaniment of the molecular oxygen by molecular nitrogen is advantageously realized in such a manner that the molecular oxygen is introduced into reaction zone B as a component of a gas which already comprises the molecular oxygen and molecular nitrogen in an abovementioned ratio R or consists only of molecular oxygen and molecular nitrogen in such a ratio R. In the process according to the invention, preference is given to at least partially, more preferably predominantly or exclusively, using air as the source for the molecular oxygen required in reaction zone B. However, it is also possible to introduce to reaction zone B, for example, air and additionally molecular oxygen or air and additional molecular nitrogen or air and additionally a mixture of molecular nitrogen and molecular oxygen which comprises the two gas components in a ratio other than that in air. It is essential to the invention only that the ratio R be maintained overall. According to the invention, molecular oxygen and molecular nitrogen could also be introduced spatially separated to the reaction zone B.

In other words, while DE-A 3313573 teaches the selective heterogeneously catalyzed partial oxidation of isobutene in reaction zone B in a reaction gas mixture which comprises in particular isobutene, isobutane and molecular oxygen, the reaction gas mixture in reaction zone B in the process according to the invention necessarily contains isobutene, isobutane, molecular oxygen and molecular nitrogen. The additional presence of the latter in the process according to the invention surprisingly ensures a reduction in the undesired conversion of isobutane to undesired by-product.

It will be appreciated that the charging gas mixture (=the mixture of all gas streams introduced into the reaction zone) of reaction zone B in the procedure according to the invention comprises, in addition to the components already mentioned, other components, for example, CO, $CO_2$, $H_2O$, noble gases such as He and/or Ar, hydrogen, methane, ethylene, ethane, butanes, butenes, butynes, pentanes, propyne, allenes, propane, propylene, acrolein and/or methacrolein.

According to the invention, the molecular nitrogen content of the charging gas mixture of reaction zone B, based on the amount of isobutene contained in this charging gas mixture, should generally not be less than 500 mol %. In other words, the molecular nitrogen content of the charging gas mixture of reaction zone B in the process according to the invention, based on the amount of isobutene present, can be at least 500 mol %, or at least 600 mol %, or at least 900 mol %. However, the ratio of the molar quantity of molecular nitrogen contained in the charging gas mixture of reaction zone B to the amount of isobutene contained in the charging gas mixture of reaction zone B according to the invention will normally be $\leq 20:1$, frequently $\leq 12:1$.

The molar ratio of the amount of molecular nitrogen contained in the charging gas mixture of reaction zone B to the amount of isobutane in the charging gas mixture of reaction zone B in the process according to the invention will generally not be less than 1:1. Normally, this ratio will also not be above 20:1.

In other words, the molar ratio of the amount of molecular nitrogen contained in the charging gas mixture of reaction zone B to the amount of isobutane contained in the charging gas mixture of reaction zone B can according to the invention be from 1:1 to 20:1, or from 2:1 to 16:1, or from 2:1 to 6:1.

Frequently, the composition of the charging gas mixture of reaction zone B in the process according to the invention will be selected in such a manner that the following molar ratios are fulfilled:

isobutane:isobutene:$N_2$:$O_2$:$H_2O$:$H_2$:others=10–40: 4–8:20–80:5–20:0–20:0–10:0–5.

According to the invention, the abovementioned molar ratios advantageously=10–25:4–8:40–80:10–15:5–15:2–6: 0.1–3.

An essential feature of the procedure according to the invention is that, in contrast to the case of a heterogeneous and/or heterogeneously catalyzed partial oxydehydrogenation of isobutane, molecular hydrogen is formed at least intermediately in reaction zone A, which is why the product gas mixture A generally comprises molecular hydrogen. Furthermore, the catalytic dehydrogenation in reaction zone A is endothermic without additional measures, while a catalytic oxydehydrogenation is exothermic. In the process according to the invention, the molar ratio of isobutene contained in the product gas mixture A to molecular hydrogen contained in the product gas mixture A will generally be $\leq 10$, customarily $\leq 5$, frequently $\leq 3$, often $\leq 2$.

Normally, the reciprocal of the abovementioned ratio will not exceed 2. In other words, the molar ratio of isobutene contained in the product gas mixture A to molecular hydrogen contained in the product gas mixture A in the process according to the invention will customarily be $\geq 0.5$, usually $\geq 0.8$, and in many cases $\leq 1.2$, or $\leq 1.5$.

In order to achieve interesting conversions in reaction zone A in the partially heterogeneously catalyzed dehydrogenation to be carried out according to the invention, based on a single pass, operation generally has to be effected at relatively high reaction temperatures (typically these reaction temperatures are from 300 to 700° C.). Since the dehydrogenation (cleavage of, C—H) is kinetically disadvantaged compared to cracking (cleavage of C—C), it is effected on selective catalysts. For every isobutene molecule formed, a hydrogen molecule is generally by-produced. As a consequence of the selective catalysts which are customarily configured in such a manner that they display significant dehydrogenation (at isobutane gas hourly space velocities of, for example, 1000 $h^{-1}$ (1 at STP/1 of cat·h), the isobutene yield is generally at least 30 mol % in a single pass (based on isobutane used)) with the exclusion of oxygen at the abovementioned temperatures (for example at 600° C.), by-products such as methane, ethylene, propane, propene and ethane are only formed in insignificant amounts.

Since the dehydrogenation reaction proceeds with decreasing volume, the conversion may be increased by reducing the partial pressure of the products. This can be achieved in a simple manner, for example, by dehydrogenating at reduced pressure and/or by admixing in substantially inert diluent gases, for example steam, which is normally an inert gas for the dehydrogenation reaction. Dilution with steam generally has the further advantage of reduced coking of the catalyst used, since the steam reacts with coke formed by the principle of coal gasification. Also, steam may be used as a diluent gas in the subsequent reaction zone B. According to the invention, it is entirely possible to use the entirety or else only a portion of the molecular nitrogen to be used in reaction zone B according to the invention also for dilution in reaction zone A. Examples of further diluents for reaction zone A include CO, $CO_2$ and noble gases such as He, Ne and Ar (however, operation in reaction zone A may in principle also be effected without diluents; i.e. the charging gas mixture of reaction zone A may consist only of isobutane or only of isobutane and molecular oxygen). All of the diluents mentioned may be used in reaction zone A either alone or in the form of highly varying mixtures. According to the invention, it is advantageous that the diluents suitable for the reaction zone A are generally also diluents suitable for reaction zone B. In general, preference is given to diluents which behave inertly (i.e. less than 5 mol %, preferably less than 3 mol % and even better less than 1 mol % are chemically altered) in each reaction zone.

In principle, all dehydrogenation catalysts known from the prior art are suitable for reaction zone A according to the invention. They can be roughly divided into two groups, i.e. those of oxidic nature (for example chromium oxide and/or aluminum oxide) and those which consist of at least one generally comparatively precious metal (for example platinum) deposited on at least one generally oxidic support.

Dehydrogenation catalysts which may be used for stage A according to the invention are, inter alia, all of those recommended by DE-A 10060099 (the example), WO 99/46039, U.S. Pat. No. 4,788,371, EP-A, 705 136, WO 99/29420, U.S. Pat. No. 5,220,091, U.S. Pat. No. 5,430,220, U.S. Pat. No. 5,877,369, DE-A 10047642, EP-A 117 146, DE-A 19 937 106, DE-A 19 937 105, DE-A 10 211 275 and also DE-A 19 937 107. In particular, all the dehydrogenation process variants mentioned in this document as being suitable for reaction zone A according to the invention may be carried out using the catalyst according to Example 1, and also according to Example 2, and also according to Example 3, and also according to Example 4 of DE-A 19 937 107.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the periodic table, of lanthanum and/or of tin, with the proviso that the sum total of the percentages by weight is 100% by weight.

The at least one catalyst bed (for example fluidized bed, moving bed or fixed bed) required for the purposes of the present invention may contain the dehydrogenation catalyst in differing geometries. Examples of useful geometries for the process according to the invention include shapes such as spall, tablets, monoliths, spheres or extrudates (rods, wagonwheels, stars, rings). In the case of extrudates, the length is advantageously from 2 to 15 mm, frequently from 2 to 10 mm, in many cases from 6 to 10 mm, and the diameter of the extrudate cross section is advantageously from 1 to 5 mm, frequently from 1 to 3 mm. In the case of rings, the wall thickness is advantageously from 0.3 to 2.5 mm, and the length is from 2 to 15 mm, frequently from 5 to 15 mm, and the diameter of the cross section from 3 to 10 mm. A suitable shaping process is disclosed, for example, by DE-A 10047642 and also DE-A 19937107. The process is based on the fact that oxidic support materials admixed with concentrated mineral acid (for example concentrated nitric acid) can be comparatively efficiently kneaded and can be converted by means of an extruder or an extrudate press to an appropriate shaped body.

The shaped bodies are then dried and calcined and then salt solutions are poured over them in a suitable sequence. Finally, they are again dried and calcined.

The reaction zone A relevant for the process according to the invention may in principle be realized in all reactor types known from the, prior art for heterogeneously catalyzed partial. dehydrogenations of hydrocarbons in the gas phase over fixed-bed catalysts. Typical reaction temperatures are from 200 to 800° C., or from 400 to 650° C. The working pressure is typically in the range from 0.5 to 10 bar. Typical gas hourly space velocities of, reaction gas are from 300 to 16 000 h$^{-1}$.

In principle, all reactor types and process variants known from the prior art may be used to embody reaction zone A of the process according to the invention. Descriptions of such process variants are contained in, for example, all prior art documents mentioned in relation to the dehydrogenation catalysts.

A comparatively comprehensive description, of dehydrogenation processes suitable according to the invention is also contained in "Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.".

A characteristic feature of the partial heterogeneously catalyzed dehydrogenation of isobutane is that it is endothermic. In other words, the heat (energy) necessary to achieve the required reaction temperature has to be supplied either in advance to the reaction gas and/or in the course of the catalytic dehydrogenation.

Also, owing to the high reaction temperatures required, it is typical of heterogeneously catalyzed dehydrogenations of isobutane that small amounts of high-boiling high molecular weight organic compounds, up to and including carbon, are formed which deposit on the catalyst surface and thus deactivate it. In order to minimize this disadvantageous side effect, it is possible, as already mentioned, to dilute with steam the isobutane to be passed over the catalyst surface at elevated temperature for catalytic dehydrogenation. Under the resulting conditions, depositing carbon is partially or completely eliminated by the principle of coal gasification.

Another possible way of removing deposited carbon compounds consists in passing an oxygen-containing gas through the dehydrogenation catalyst at elevated temperature from time to time and effectively burning off the deposited carbon. However, it is also possible to suppress carbon deposit formation by adding molecular hydrogen to the isobutane to be catalytically dehydrogenated before it is passed over the dehydrogenation catalyst at elevated temperature.

It will be appreciated that the possibility also exists of adding a mixture of steam and molecular hydrogen to the isobutane to be catalytically dehydrogenated. Addition of molecular hydrogen to the catalytic dehydrogenation of isobutane also reduces the undesired formation of by-produced allene, acetylene and other carbon precursors.

In the majority of processes known for heterogeneously catalyzed partial dehydrogenation of hydrocarbons such as isobutane to be dehydrogenated, the heat of dehydrogenation is generated outside the reactor and supplied to the reaction gas from outside. However, this requires complicated reactor and process concepts and lead, particularly at high conversions, to steep temperature gradients in the reactor with the general disadvantage of increased by-product formation.

Alternatively, the heat of dehydrogenation may also be generated directly in the reaction gas itself by adding molecular oxygen and exothermically combusting hydrogen formed either in the dehydrogenation or supplied additionally to give steam. To this end, a molecular oxygen-containing gas and optionally hydrogen are added to the reaction gas before and/or after entrance into the reaction zone containing the dehydrogenation catalyst. Either the dehydrogenation catalyst itself (this applies to most dehydrogenation catalysts) and/or any additionally installed oxidation catalysts generally ease the desired hydrogen oxidation (cf. DE-A 10028582). In favorable cases, heat of reaction released in this manner by means of hydrogen combustion allows indirect reactor heating to be completely dispensed with and accordingly comparatively simple process concepts and also limited temperature gradients in the reactor even at high conversions.

In the above procedure, the use of external molecular hydrogen may, for example, be avoided when the process principle of DE-A 10 211 275 is applied.

According to this process principle, a reaction gas containing the at least one hydrocarbon to be dehydrogenated (isobutane in this case) is continuously introduced into the catalytic dehydrogenation zone (reaction zone A in this case). In the catalytic dehydrogenation zone, the reaction gas is passed over at least one fixed catalyst bed where molecular hydrogen and some of at least one dehydrogenated hydrocarbon (isobutene in this case) are formed by catalytic dehydrogenation. Before and/or after entry into the catalytic dehydrogenation zone, at least one molecular oxygen-containing gas which at least partially oxidizes the molecular hydrogen contained in the reaction gas in the catalytic dehydrogenation zone to give steam is added to the reaction gas. A product gas mixture is then withdrawn from the catalytic dehydrogenation zone which comprises molecular hydrogen, steam, the at least one dehydrogenated hydrocarbon and the at least one hydrocarbon to be dehydrogenated, divided into two portions of identical composition and one of the two portions is returned to the catalytic dehydrogenation zone (cycle gas) as the source for molecular hydrogen. In the process according to the invention, the other portion would be introduced as product gas mixture A into reaction zone B.

It will be appreciated that reaction zone A in the process according to the invention may also be configured in such a manner that there is a further fixed catalyst bed downstream of the dehydrogenation catalyst fixed bed in the flow direction of the reaction gas where molecular hydrogen contained in the reaction gas is at least partially combusted to steam by selective heterogeneous catalysis so that the product gas mixture A in the process according to the invention may be substantially or completely free of hydrogen. Catalysts suitable for this purpose are disclosed by, for example, U.S. Pat. No. 4,788,371, U.S. Pat. No. 4,886,928, U.S. Pat. No. 5,430,209, U.S. Pat. No. 55,530,171, U.S. Pat. No. 5,527, 979, EP-A 832056 and U.S. Pat. No. 5,563,314. Subsequent cooling in reaction zone A may be used to condense out steam contained in the gas mixture (and, if required, to recycle it into reaction zone A) and thus to obtain a substantially steam-free product gas mixture A. Further-reaching removals should not be carried out on the route to the product gas mixture A for the purposes of the present invention.

A useful reactor form for reaction zone A according to the invention is the fixed bed tubular or tube bundle reactor. In other words, the dehydrogenation catalyst and any specific hydrogen oxidation catalyst, as disclosed, for example, in the documents U.S. Pat. No. 4,788,372, U.S. Pat. No. 4,886,928, U.S. Pat. No. 5,430,209, U.S. Pat. No. 5,550,171, U.S. Pat. No. 5,527,979, U.S. Pat. No. 5,563,314 and EP-A 832056 is disposed in a reaction tube or in a bundle of reaction tubes as a fixed bed. The reaction tubes are customarily indirectly heated by combusting a gas, for example a hydrocarbon such as methane, in the space surrounding the reaction tubes. It is advantageous to apply this indirect form of heating only to the first 20 to 30% of the fixed bed and to heat the remaining bed length to the required reaction temperature using the radiative heat released in the combustion. Indirect heating of the reaction gas may be combined advantageously with direct heating by combustion with molecular oxygen in the reaction gas. In this manner, a virtually isothermal reaction is achievable in a comparatively simple form. Suitable reaction tube internal diameters are from about 10 to 15 cm. A typical dehydrogenation bundle tube reactor comprises from 300 to 1000 reaction tubes. The temperature in the reaction tube interiors is in the range from 300 to 700° C., preferably in the range from 400 to 700° C. The working pressure is customarily in the range from 0.5 to 8 bar, frequently from 1 to 2 bar or else from 3 to 8 bar. Advantageously, the reaction gas is introduced into the tubular reactor preheated to the reaction temperature. In general, the product gas mixture leaves the reaction tube at a (higher or lower) temperature other than the entrance temperature (cf. also U.S. Pat. No. 4,902,849, U.S. Pat. No. 4,996,387 and U.S. Pat. No. 5,389,342). For the purposes of the abovementioned procedure, it is advantageous to use oxidic dehydrogenation catalysts based on chromium oxide and/or aluminum oxide. Frequently, no diluent gas will be used, and instead substantially pure isobutane will be used as the starting reaction gas. The dehydrogenation catalyst is usually also used undiluted.

Typical isobutane gas hourly space velocities are from 500 to 2000 $h^{-1}$ (=1 at STP/1 of catalyst·h).

On the industrial scale, about three tube bundle reactors would be operated in parallel, two of which would generally be carrying out dehydrogenation, while one of the reactors regenerates the catalyst charge.

It will be appreciated that reaction zone A according to the invention can also be configured within a moving bed. For example, the moving catalyst bed may be accommodated in a radial flow reactor. In this, the catalyst moves gradually from top to bottom while the reaction gas mixture flows radially. This procedure is used, for example, in the UOP Oleflex dehydrogenation process. Since the reactors in this process are operated virtually adiabatically, it is advantageous to operate more than one reactor in series (typically up to four). This allows excessively high differences in the temperatures of the reaction gas mixture at the reactor entrance and reactor exit to be avoided (in the adiabatic mode, the starting reaction gas mixture functions as a heat carrier on whose heat content the reaction temperature is dependent) and, despite this, attractive overall conversions to be achieved.

When the catalyst bed has left the moving bed reactor, it is regenerated and then reused. An example of a dehydrogenation catalyst for this process is a spherical dehydrogenation catalyst which consists substantially of platinum on a spherical aluminum oxide support. In order to avoid premature catalyst aging, hydrogen is advantageously added to the isobutane to be dehydrogenated. The working pressure is typically from 1 to 5 bar. The hydrogen to isobutane (molar) ratio is advantageously from 0.1 to 1. The reaction temperatures are preferably from 550 to 650° C. and the gas hourly space velocity of reaction gas mixture is from about 200 to 1000 $h^{-1}$. The catalyst charge may also consist of a mixture of dehydrogenation and $H_2$ oxidation, catalysts, as recommended by EP-A 832056.

In the fixed bed processes described, the catalyst geometry may likewise be spherical, or else cylindrical (hollow or solid).

A further process variant for: reaction zone A according to the invention is described by Proceedings De Witt, Petrochem. Review, Houston Tex., 1992 a, N1, which contemplates the possibility of a heterogeneously catalyzed dehydrogenation in a fluidized bed without diluting the isobutane.

This variant advantageously involves operating two fluidized beds in parallel, of which one is generally in the process of regeneration. The active composition used is chromium oxide on aluminum oxide. The working pressure is typically from 1 to 1.5 bar and the dehydrogenation temperature is generally from 550 to 600° C. The heat required for the dehydrogenation is introduced into the reaction system by preheating the dehydrogenation catalyst to the reaction temperature. The working pressure is regularly from 1 to 2 bar and the reaction temperature typically from 550 to 600° C. The above dehydrogenation method is also disclosed in the literature as the Snamprogetti-Yarsintez process.

As an alternative to the above-described procedures, reaction zone A according to the invention may also be realized according to a process developed by ABB Lummus Crest (cf. Proceedings De Witt, Petrochem. Review, Houston Tex., 1992, P1).

Common to the heterogeneously catalyzed dehydrogenation processes for isobutane described hitherto is that they are operated at isobutane conversions of >30 mol % (in general $\leq$70 mol %) (based on single reactor pass).

An advantage of the present invention is that it is sufficient for the process according to the invention for an isobutane conversion of from $\geq$5 mol % to $\leq$30 mol % or $\leq$25 mol % to be achieved in reaction zone A. In other words, reaction zone A may also be operated at isobutane conversions of from 10 to 30 mol % according to the invention (the conversions relate to single reactor pass). Among other factors, this results from the dilution with molecular nitrogen of the remaining amount of unconverted isobutane in the downstream reaction zone B which reduces the by-production of isobutyraldehyde and/or isobutyric acid.

To realize the abovementioned isobutane conversions, it is advantageous to carry out the isobutane dehydrogenation according to the invention in reaction zone A at a working pressure of from 0.3 to 3 bar. It is further advantageous to dilute the isobutane to be dehydrogenated with steam. On the one hand, the heat capacity of the water allows the endothermic effect of the dehydrogenation to be partially compensated for and, on the other hand, dilution with steam reduces the reactant and product partial pressures, which has an advantageous effect on the dehydrogenation equlibrium location. In addition, the concomitant use of steam, as already mentioned, has an advantageous effect on the onstream time of the dehydrogenation catalyst. If required, molecular hydrogen may also be added as a further component. The molar ratio of molecular hydrogen to isobutane is generally $\leq$5. The molar ratio of steam to isobutane in the reaction zone A variant with comparatively low isobutane conversion may accordingly be from $\geq$0 to 30, conveniently from 0.1 to 2 and advantageously from 0.5 to 1. It has also proven advantageous for a procedure with low isobutane conversion that only a comparatively low heat quantity is consumed in single reactor pass of the reaction gas and comparatively low temperatures are sufficient to achieve the conversion in single reactor pass.

According to the invention, it is therefore advantageous in the reaction zone A variant with comparatively low isobutane conversion to carry out the isobutane dehydrogenation (quasi) adiabatically. In other words, the starting reaction gas mixture will generally be heated to a temperature of from 500 to 700° C. (for example by direct firing of the wall surrounding it in a heater), or to from 550 to 650° C. Normally, a single adiabatic pass through a catalyst bed will then be sufficient to achieve the desired conversion, and the reaction gas mixture will cool by from about 30° C. to 200° C. (depending on the conversion). The presence of steam as a heat carrier is also advantageous from the point of view of an adiabatic method. The relatively low reaction temperature allows relatively long on-stream times of the catalyst bed used.

In principle, the reaction zone A variant according to the invention having comparatively low isobutane conversion, whether performed adiabatically or isothermally, may also be carried out either in a fixed bed reactor or else in a moving bed or fluidized bed reactor.

Remarkably, a single shaft furnace reactor as the fixed bed reactor, through which the reaction gas mixture flows axially and/or radially, is sufficient to realize this variant, particularly in adiabatic operation.

In the simplest case, this reactor is a single reaction tube whose internal-diameter is from 0.1.to 10 m, possibly also from 0.5 to 5 m, where the fixed catalyst bed is mounted on a supporting device (for example a grid). The reaction tube charged with catalyst which may be heat-insulated in adiabatic operation is flowed through axially by the hot, isobutane-containing reaction gas. The catalyst geometry may be either spherical, extruded or annular. However, the catalyst may advantageously also be used in the abovementioned case in the form of spall. To realize radial flow of the isobutane-containing reaction gas, the reactor may consist, for example, of two concentric cylindrical-grids disposed in a jacket and the catalyst bed may be arranged in the annular gap between them. In the adiabatic case, the jacket would in turn be thermally insulated.

Useful catalyst charges for the reaction zone A variant according to the invention with comparatively low isobutane conversion in a single pass are in particular the catalysts disclosed by DE-A 19 937 107, above all those disclosed by way of example.

After a relatively long operation time, the abovementioned catalysts can be regenerated, for example, in a simple manner by initially passing nitrogen- and/or steam-diluted air over the catalyst bed in first regeneration stages at a temperature of from 300 to 900° C., frequently from 400 to 800° C., often from 500 to 700° C. The gas hourly space velocity of regeneration gas may be, for example, from 50 to 10 000 h$^{-1}$ and the oxygen content of the regeneration gas may be from 0.5 to 20% by volume.

In the further downstream regeneration stages, air may be used as the regeneration gas under otherwise identical regeneration conditions. It has proven advantageous from an application point of view to purge the catalyst before regeneration with inert gas (for example N$_2$).

It is then generally recommended to regenerate further with pure molecular hydrogen or with molecular hydrogen diluted with inert gas (the hydrogen content should be ≧1% by volume) under otherwise identical conditions. Frequently, it is advantageous to carry out the regeneration procedure twice or more in succession.

The reaction zone A variant according to the invention with comparatively low isobutane conversion (≦30 mol %) may in all cases be operated at the same gas hourly space velocities (relating both to the overall reaction gas and to the isobutane contained therein) as the variants with high isobutane conversion (>30 mol %). This gas hourly space velocity of reaction gas may be, for example, from 100 to 10 000 h$^{-1}$, frequently from 100 to 3000 h$^{-1}$, i.e. in many cases from 100 to 2000 h$^{-1}$.

In a particularly elegant manner, the reaction zone A variant according to the invention with comparatively low isobutane conversion can be realized in a tray reactor.

This comprises more than one catalyst bed catalyzing the dehydrogenation in spatial succession. The catalyst bed number may be from 1 to 20, advantageously from 2 to 8 but also from 4 to 6. The catalyst beds are preferably arranged in radial or axial succession. From an application point of view, it is advantageous to used the fixed catalyst bed type in such a tray reactor.

In the simplest case, the fixed catalyst beds in a shaft furnace reactor are arranged axially or in the annular gaps of concentric cylindrical grids.

Advantageously, the reaction gas mixture will be subjected to intermediate heating in the tray reactor on its way from one catalyst bed to the next catalyst bed, for example by passing it over heat exchanger ribs heated by hot gases or by passing it through pipes heated by hot combustion gases.

When the tray reactor is otherwise operated adiabatically, it is sufficient for the desired isobutane conversions (≦30 mol %), in particular when the catalysts described in DE-A 19 937 107, in particular those of the exemplary embodiments, are used, to pass the reaction gas mixture into the dehydrogenation reactor preheated to a temperature of from 450 to 550° C. and to maintain it within this temperature range inside the tray reactor. In other words, the entire isobutane dehydrogenation can thus be realized at very low temperatures, which is particularly advantageous for the onstream time of the fixed catalyst beds.

It is even more beneficial to carry out the above-described intermediate heating in a direct way. To this end, a limited amount of molecular oxygen or a gas containing it is added to the reaction gas mixture either before it flows through the first catalyst bed and/or between the subsequent catalyst beds. Depending on the dehydrogenation catalyst used, a limited combustion of the hydrocarbons contained in the reaction gas mixture, any coke or coke-like compounds already deposited on the catalyst surface and/or hydrogen formed in the course of the isobutane dehydrogenation and/or added to the reaction mixture is thus effected (it may also be advantageous from an application point of view to add catalyst beds in the tray reactor which are charged with catalyst which specifically (selectively) catalyzes the combustion of hydrogen (and/or of hydrocarbon) (examples of useful catalysts include those of the documents U.S. Pat. No. 4,788,371, U.S. Pat. No. 4,886,928, U.S. Pat. No. 5,430,209, U.S. Pat. No. 55,530,171, U.S. Pat. No. 5,527,979 and U.S. Pat. No. 5,563,314); for example, such catalyst beds could be accommodated in the tray reactor in alternation to the beds containing the dehydrogenation catalyst). The heat of reaction released thus allows virtually isothermal operation of the heterogeneously catalyzed isobutane dehydrogenation in a quasi-autothermal manner. As the selected residence time of the reaction gas in the catalyst bed is increased, isobutane dehydrogenation is thus possible at decreasing and substantially constant temperature which allows particularly long onstream times.

In general, oxygen feeding as described above should be carried out in such a manner that the oxygen content of the reaction gas mixture, based on the amount of isobutane and isobutene contained therein, is from 0.5 to 10% by volume. Useful oxygen sources include both pure molecular oxygen and oxygen diluted with inert gas, for example CO, $CO_2$, $N_2$ or noble gases, but in particular also air. The resulting combustion gases generally have an additional dilution effect and thus support the heterogeneously catalyzed isobutane dehydrogenation.

The dehydrogenation temperature in the tray reactor in the process according to the invention is generally from 400 to 800° C., and the pressure is generally from 0.2 to 10 bar, preferably from 0.5 to 4 bar and more preferably from 1 to 2 bar. The gas hourly, space velocity is generally from 500 to 2000 $h^{-1}$, and in high-load operation even up to 16 000 $h^{-1}$, regularly from 4000 to 16 000 $h^{-1}$.

The isothermicity of the heterogeneously catalyzed isobutane dehydrogenation can be further improved by incorporating closed internals (for example tubular) which have been evacuated before filling in the spaces between the catalyst beds in the tray reactor. It will be appreciated that such internals may also be placed in each catalyst bed. These internals contain suitable solids or liquids which evaporate or melt above a certain temperature, thereby consuming heat, and, when the temperature falls below this value, condense again and thereby release heat.

Another possible method of heating the reaction gas mixture to the required temperature in reaction zone A of the process according to the invention consists in combusting a portion of the isobutane and/or $H_2$ contained therein using molecular oxygen (for example over specific combustion catalysts for example by simply passing them over and/or through) and to effect the heating to the desired reaction temperature by means of the heat of combustion released in this manner. The resulting combustion products such as $CO_2$, $H_2O$ and also any $N_2$ accompanying the molecular oxygen required for the combustion advantageously take on the role of inert diluent gases.

It will be appreciated that reaction zone A according to the invention can also be realized in a jet pump circulation reactor as described by DE-A 10 211 275. Quite generally, all dehydrogenation variants described in DE-A 10 211 275 are usable in reaction zone A according to the invention.

It is essential to the invention that the isobutane used in reaction zone A is not pure isobutane. Rather, the isobutane used may comprise up to 50% by volume of other gases, for example, ethane, methane, ethylene, n-butanes, n-butenes, propyne, acetylene, propane, propene, $H_2S$, $SO_2$, pentanes, etc. Advantageously, the crude isobutane to be used comprises at least 60% by volume, advantageously at least 70% by volume, preferably at least 80% by volume, more preferably at least 90% by volume and most preferably at least 95% by volume, of isobutane. In particular, a mixture of isobutane, isobutene and cycle gas arising from reaction zone B may also be used for reaction zone A according to the invention.

The product gas mixture A leaving reaction zone A in the process according to the invention comprises at least the components isobutane and isobutene, and also generally molecular hydrogen. Furthermore, it will generally also comprise gases from the group consisting of $N_2$, $H_2O$, methane, ethane, ethylene, propane, propene, CO and $CO_2$ and also possibly $O_2$.

The mixture will generally be at a pressure of from 0.3 to 10 bar and frequently a temperature of from 450 to 500° C. Quite generally, reactors having passivated interior walls are used for reaction zone A according to the invention. The passivation may be effected, for example, by applying sintered aluminum oxide to the interior wall before dehydrogenation or by using a silicon-containing steel as the reactor material which forms a passivating $SiO_2$ layer on the surface under the reaction conditions. However, passivation may also be achieved in situ by adding small quantities of passivating auxiliaries (for example sulfides) to the reaction zone A charging gas mixture.

The product gas mixture A leaving reaction zone A, which comprises isobutane and isobutene, is used according to the inventive procedure to charge a reaction zone B in order to subject the isobutylene to a selective heterogeneously catalyzed gas phase partial oxidation using molecular oxygen in the reaction zone to obtain a methacrolein-containing product gas mixture. If required, the product gas mixture A may be brought in advance by indirect heat exchange to the reaction temperature required in reaction zone B.

Appropriate multimetal oxide catalysts to be used in reaction zone B have been described many times before and are well known to those skilled in the art. In general, preference is given according to the invention to catalysts based on multimetal oxides comprising the element combination Mo—Bi—Fe.

For example, U.S. Pat. No. 4,954,650, U.S. Pat. No. 5,166,119, DE-A 10 121 592 (multimetal oxide compositions of the formulae I, II and III in the same DE-A), DE-A 10 046 957 (multimetal oxide compositions of the formulae I and II in the same DE-A), DE-A 10 101 695 (multimetal oxide compositions of the formulae I, II and III in the same DE-A), DE-A 10 063 162 (multimetal oxide compositions of the formula I in the same DE-A), DE-A 10 059 713 (multimetal oxide compositions of the formula I in the same DE-A) and DE-A 10 049 873 (multimetal oxide compositions of the formula I in the same DE-A) disclose multimetal oxide catalysts suitable for reaction zone B.

A variety of multimetal oxide compositions suitable as catalysts for the reaction zone B can be subsumed by the general formula I

$$Mo_{12}Bi_aFe_bX^1_cX^2_dX^3_eX^4_fO_n \qquad (I),$$

where the variables are defined as follows:
$X^1$=nickel and/or cobalt,
$X^2$=an alkali metal, thallium and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements other than oxygen in I.

The compositions are obtainable in a manner known per se (cf., for example, DE-A 10 121 592) and are customarily used as such shaped into spheres, rings, cylinders or else in the form of coated catalysts, i.e. preshaped inert support particles coated with the active composition.

Examples of suitable unsupported catalyst geometries include solid cylinders and hollow cylinders having an external diameter and a length of from 2 to 10 mm. In the case of the hollow cylinders, a wall thickness of from 1 to 3 mm is advantageous. It will be appreciated that the unsupported catalyst may also have spherical geometry and the sphere diameter may be from 2 to 10 mm. Useful coated catalyst geometries are likewise disclosed by DE-A 10 121 592.

According to the invention, further multimetal oxide compositions useful as catalysts for reaction zone B are compositions of the general formula II

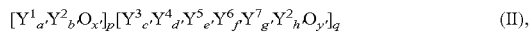

$$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad \text{(II),}$$

where the variables are defined as follows:
$Y^1$=only bismuth or bismuth and at least one of the elements tellurium, antimony, tin and copper,
$Y^2$=molybdenum and/or tungsten,
$Y^3$=an alkali metal, thallium and/or samarium,
$Y^4$=an alkaline earth metal, nickel, cobalt, copper, manganese, zinc, tin, cadium and/or mercury,
$Y^5$=iron or iron and at least one of the elements chromium, cerium and vanadium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'>[sic] from 0 to 20,
f'=from 0 to 6,
g'=from 0 to 15,
h'=from 8 to 16,
x',y'=numbers which are determined by the valency and frequency of elements other than oxygen in II and
p,q=numbers whose ratio p/q is 0.1 to 10.

In favorable cases, the multimetal oxide compositions II comprise three-dimensional regions which are delimited from their local environment owing to their different composition from their local environment and of the chemical composition $Y^1_{a}Y^2_{b}O_{x'}$ and whose maximum diameter (longest line connecting two points on the surface (boundary layer) of the region and passing through the main focus of the region) is from 1 nm to 100 μm, frequently from 10 nm to 500 nm or from 1 μm to 50 or 25 μm.

With regard to the shaping, the remarks made on multimetal oxide compositions I catalysts apply to multimetal oxide compositions II catalyts.

The preparation of multimetal oxide compositions II catalysts is described, for example, by EP-A 575897, DE-A-19855913, DE-A 10 046 957 and DE-A 10 121 592.

Reaction zone B is most easily realized by a tube-bundle reactor whose catalyst tubes are charged with catalyst. The configuration may be entirely similar to the teaching of EP-A 911313, EP-A 979813, EP-A 990636 and DE-A 2830765 for the partial oxidation of propylene to acrolein. Otherwise, reaction zone B may be configured as taught in U.S. Pat. No. 4,954,650 and U.S. Pat. No. 5,166,119.

The reaction temperature is generally-from 250 to 450° C. The reaction pressure is advantageously from 0.5 to 5, frequently from 1 to 3, bar. The gas hourly space velocity (1 at STP/1·h) on the oxidation catalysts is frequently from 1500 to 2500 h$^{-1}$ or 4000 h$^{-1}$.

In principle, reaction zone B may also be configured as described for similar reactions, for example, in DE-A 19837517, DE-A 19910506, DE-A 19910508 and also DE-A 19837519.

Customarily, the external heating, if appropriate in multizone reactor systems, is adjusted in a manner known per se to the specific reaction gas mixture composition and also catalyst charge.

The molecular oxygen required in the reaction zone B necessary for the invention is normally added in advance in its entirety to the charging gas mixture of reaction zone B.

Normally, a molar isobutene molecular oxygen ratio in the charging gas for reaction zone B of from 1:1 to 3, frequently from 1:1.5 to 2.5, is set.

An excess (based on the stoichiometry of the gas phase partial oxidation) of molecular oxygen generally has an advantageous effect on the kinetics of the gas phase oxidation in reaction zone B. In contrast to the conditions in the reaction zone A to be applied according to the invention, the thermodynamic ratios in reaction zone B are substantially not influenced by the molar reactant ratio, since the heterogeneously catalyzed gas phase partial oxidation of isobutene to methacrolein is under kinetic control.

In principle, it is therefore also possible, for example, to initially charge the isobutene into reaction zone B in a molar excess relative to the molecular oxygen. In this case, the excess isobutene actually assumes the role of a diluent gas.

A useful source for the molecular oxygen required overall in reaction zone B which is normally admixed with product gas mixture A before it is used to charge reaction zone B is in particular oxygen diluted with molecular nitrogen.

Advantageously, air will be used as the oxygen source at least to cover part of the need for molecular oxygen, since the nitrogen also to be used in reaction zone B may be introduced into the reaction system in this manner in a very simple way.

However, a portion of the molecular oxygen required overall in reaction zone B may also already be contained in the product gas mixture A introduced into reaction zone B. Preference is given to no oxygen being contained in the product gas mixture A. Further useful oxygen sources usable in the reaction zone include molecular oxygen diluted with inert gases such as $CO_2$, CO, noble gases, $N_2$ and/or saturated hydrocarbons. An example of such an oxygen source is a cycle gas diverted from the process according to the invention and recycled into reaction zone B.

In the process according to the invention, the source for molecular oxygen in the downstream reaction zone B, apart from any molecular oxygen already contained in the product gas mixture A, is advantageously at least partially and preferably exclusively air.

The metering of cold air at room temperature into the hot product gas mixture A in the process according to the invention may also be directly used to cool the product gas mixture A on its way into reaction zone B.

The product gas mixture B leaving reaction zone B to be used according to the invention is generally substantially composed of the target product methacrolein or a mixture thereof with methacrylic acid, unconverted molecular oxygen, isobutane, unconverted isobutene, molecular nitrogen, molecular hydrogen, hydrogen formed as a by-product and/or used as a diluent gas, carbon oxides as a by-product and/or used as a diluent gas, and also small amounts of other lower aldehydes, hydrocarbons and other inert diluent gases. However, the isobutyraldehyde and isobutyric acid contents are minimized in accordance with the invention. When the target product which is eventually desired is not methacrolein but methacrylic acid, it is possible, as recommended by DE-A 3313573, to conduct the methacrolein-containing product gas mixture as such into a reaction zone C and to subject the methacrolein to a selective catalyst partial oxidation in reaction zone C in the gas phase using molecular oxygen to form a methacrylic acid-containing product gas mixture C.

Advantageous catalysts for such a reaction zone C are disclosed, for example, by DE-A 44 05 060, U.S. Pat. No. 5,166,119, U.S. Pat. No. 5,153,162, U.S. Pat. No. 4,954,650, U.S. Pat. No. 4,558,028 and DE-A 19 815 279. These patents also teach the use of such catalysts. In general, preference is generally given to catalysts based on multimetal oxides comprising the element combination Mo—P. As well as molybdenum and phosphorus, they customarily comprises metallic and transition metallic elements, in particular copper, vanadium, arsenic, antimony, cesium and also potassium (cf. DE-A 4329907, DE-A 2610249, JP-A 7/185354).

DE-A 19922113 suggests multimetal oxide compositions of the general formula III $$[A]_p [B]_q \quad (III),$$

where the variables are defined as follows:
A: $Mo_{12}X_z^1 X_b^2 X_c^3 X_d^4 X_e^5 O_x$
B: $Mo_f X_g^6 X_h^7 O_y$
$X^1$=H, of which up to 97 mol % may be replaced by ammonium, K, Rb, and/or Cs,
$X^2$=V, Nb, Ta, W and/or Re,
$X^3$=B, Si, P, Ge, As and/or Sb,
$X^4$=Cr, Fe, Co, Ni, Cu, Zn, Mg, Ca, Sr and/or Ba,
$X^5$=S,
$X^6$=Cu, Fe, Co, Ni, Zn, Cd, Mn, Mg, Ca, Sr and/or Ba,
$X^7$=Nb, Ta and/or Sb,
a=from 1 to 3,
b=from 0.1 to 2,
c=from 0 to 5,
d=from 0 to 1,
e=from 0 to 1,
f=from 0 to 2,
g=from 0.5 to 1.5,
h=from 2 to 4,
x,y=numbers which are determined by the valency and frequency of the elements other than oxygen in (I),
p=1 and q=0 or
p,q=are,integers other than zero whose ratio p/q is from 160:1 to 1:1 and the standard deviation of the stoichiometric coefficients a of the $X^1$ variables of individual crystallites within the component A of the multimetal oxide composition is less than 0.40, preferably less than 0.20, in particular less-than 0.11.

The compositions preferably comprise the fraction $[A]_p$ in the form of three-dimensional regions A of chemical composition A which are delimited from their local environment owing to their different chemical composition and the fraction $[B]_q$ in the form of three-dimensional regions B of chemical composition B which are delimited from their local environment owing to their different chemical composition from their-local environment, and the regions A and B are distributed relative to each other as in a finely divided mixture of A and B.

DE-A 4405060 recommends similar multimetal oxide-compositions for a reaction zone C. Like the multimetal oxide catalysts for reaction zone B, the multimetal oxide catalysts for reaction zone C are customarily used as such shaped into spheres, rings or cylinders or else in the form of coated catalysts, i.e. preformed inert support particles coated with the active composition.

Examples of suitable unsupported catalyst, geometries include solid cylinders and hollow cylinders having an external diameter and a length of from 2 to 10 mm. In the case of the hollow cylinders, a wall thickness of from 1 to 3 mm is advantageous. It will be appreciated that the unsupported catalyst may also have spherical geometry and the sphere diameter may be from 2 to 10 mm. Examples of useful coated catalyst geometries are those disclosed by DE-A 10121592.

The simplest way of realizing reaction zone, C, as in the case of reaction zone B, is a tube bundle reactor, and so all remarks made in relation to the tube bundle reactor of reaction zone B are also similarly valid for a tube bundle reactor of reaction zone C.

With regard to the flow of reaction gas and heating medium (for example salt bath), the tube bundle reactors recommended for both reaction zone B and reaction zone C may be operated either in cocurrent or else in countercurrent. It will be appreciated that crosscurrent flows may also be superimposed. A meandering flow of the temperature medium around the catalyst tubes is particularly advantageous and, viewed over the reactor, may again be in cocurrent or in countercurrent to the reaction gas mixture.

A particularly simple way of realizing the reaction zones B and C is accordingly a tube bundle reactor within which the catalyst charge changes correspondingly along the individual catalyst tubes. The charge of the catalyst tubes with catalyst may optionally be interrupted by an inert bed (EP-A 911313, EP-A 979813, EP-A 990636 and DE-A 2830765 teach such a procedure in an equivalent manner using the example of partial oxidation of propylene to acrylic acid). In the case of this way of realization, the molecular oxygen required in reaction zone C already has to be contained in the charging gas mixture for reaction zone B.

However, preference is given to realizing the two reaction zones B and C in the form of two tube bundle systems connected in series. These may optionally be in one reactor and one tube bundle may be connected to the other tube bundle by a bed (advantageously accessible on foot) of inert material which is not accommodated in the catalyst tubes. While the catalyst tubes are generally purged through by a heat carrier, this does not reach an inert bed installed as described above. However, the two catalyst tube bundles will advantageously be accommodated in spatially separated reactors. There may be an intermediate cooler between the two tube bundle reactors in order to reduce any continued methacrolein combustion in the product gas mixture which leaves reaction zone B. Instead of tube bundle reactors, plate heat exchanger reactors having salt and/or evaporative cooling, as described, for example, by DE-A 19929487 and DE-A,10952964, may also be used.

The reaction, temperature in reaction zone C is generally from 230 to 350° C., frequently from 250 to 320° C. The reaction pressure in reaction zone C is advantageously from 0.5 to 5, frequently from 1 to 3 or 2, bar. The gas hourly space velocity (1 at STP/1·h) of the oxidation catalysts of reaction C with charging gas mixture is frequently from 1000 to 2500 $h^{-1}$ or to 4000 $h^{-1}$.

As already mentioned, the molecular oxygen required overall as an oxidizing agent in reaction zone C may already be added in advance to the charging gas mixture of reaction zone B in its entirety. However, it will be appreciated that supplementation with oxygen may also be effected after reaction zone B. The last possibility,is used in particular when the two reaction zones B and C are realized in the form of two tube bundle systems in series.

Since the molecular oxygen used in reaction zone B is also a component of the charging gas mixture of reaction zone C, such oxygen supplementation may be carried out by means of pure molecular oxygen. A further oxygen source usable for such supplementation purposes is molecular oxygen diluted with inert gases such as $CO_2$, CO, noble gases, $N_2$ and/or saturated hydrocarbons. An example of such an oxygen source may be a cycle gas diverted from the process according to the invention and recycled into reaction zone C. According to the invention, preference is given to using air for such oxygen supplementation.

Even in reaction zone C, an excess (based on the reaction stoichiometry) of molecular oxygen generally has an advantageous effect on the kinetics of the gas phase oxidation. Preference is given to setting a molar methacrolein molecular oxygen ratio in reaction zone C of from 1:1 to 3, frequently from 1:1.5 to 2.5.

Frequently, the process according to the invention is carried out in such a manner sat [sic] at least 50 mol %, preferably at least 60 mol %, of the total amount of molecular oxygen in the product gas mixture C which has been introduced in the various reaction zones has been converted.

Frequently, the process according to the invention in reaction zone C will be performed at a molar methacrolein: molecular oxygen:steam:isobutane:molecular nitrogen:other diluent gas ratio of 2–6:2–20:5–30:0–40:20–80:0–6.

However, reaction zones B and C may in principle also be combined into a single reaction zone. In this case, the two reaction steps (isobutene→methacrolein; methacrolein→methacrylic acid) are effected in an oxidation reactor which is charged with a catalyst which is able to catalyze the reaction of both reaction steps. It will be appreciated that the catalyst charge within such a combined oxidation zone may also change continuously or abruptly along the reaction coordinate.

The metering of cold air (at ambient temperature) into the hot product gas mixture B in the process according to the invention may also be used as a direct way of cooling the product gas mixture B before it is used to charge reaction zone C.

The product gas mixture C leaving reaction zone C is generally composed substantially of methacrylic acid, methacrolein, unconverted molecular oxygen, isobutane, molecular nitrogen, steam formed as a by-product and/or used as a diluent gas, molecular hydrogen, carbon oxides formed as a by-product and/or used as a diluent gas, and also small quantities of other lower aldehydes, hydrocarbons and other inert diluent gases. Its isobutyraldehyde and isobutyric acid contents are minimized in accordance with the invention.

The methacrylic acid may be removed from the product gas mixture C in a manner known per se.

For example, product gas mixture C (which may have an exit temperature of, for example, 220° C.) may first be cooled by direct contact with a 10% by weight aqueous solution of methacrylic acid which may be polymerization-inhibited, for example, by the addition of small amounts of hydroquinone monomethyl ether (MEHQ) and have a temperature of 80° C. To this end, the aqueous methacrylic acid solution is sprayed in an apparatus substantially free of internals into the product gas mixture C and passed in cocurrent with it. Mist which forms may be separated from the gas phase in two Venturi precipitators. Afterwards, the cooled product gas mixture is then passed into the bottom of an absorption column, for example a randomly packed column. At the top of the column, water which contains the polymerization inhibitors dissolved is added as the absorbing liquid in countercurrent to the rising gas. The top temperature may be, for example, 63° C. and the bottom temperature, for example, 70° C.

Together with medium- and high-boiling by-products such as acetic, propionic, acrylic, maleic, fumaric, citraconic and formic acid, and also formaldehyde and any isobutyraldehyde and isobutyric a acid formed, the methacrylic acid is removed in the absorber from the gas phase into the aqueous phase.

The methacrylic acid can be removed extractively from the from 10 to 20% by weight aqueous methacrylic acid solution withdrawn from the bottom of the absorber using suitable extractants, for example ethylhexanoic acid, and subsequently isolated rectificatively.

The residual gas leaving the absorber at the top generally comprises isobutane, isobutene, methacrolein, $O_2$, $H_2$, $N_2$, CO, $CO_2$, $H_2O$, noble gases and also other lower aldehydes and, hydrocarbons.

The methacrolein can be removed therefrom by means of subsequent scrubbing with water and freed again from the scrubbing water by stripping using air and recycled with the air into reaction zone C.

Otherwise, the isobutane and isobutene contained in the residual gas remaining after the methacrylic acid removal may be substantially removed in a high-boiling hydrophobic organic solvent from other gases contained therein such as $O_2$, $H_2$, $N_2$, CO, $CO_2$, noble gases, etc. by absorption with subsequent desorption and/or stripping and also absorbent reuse, and recycled into reaction zone A. If required, the remaining other gases from the mixture may be recycled as diluent gas into reaction zones A, B and/or C.

In general, solvents useful as absorbents for the abovementioned purpose include relatively nonpolar organic solvents, for example aliphatic hydrocarbons, which preferably have no external polar groups and also aromatic hydrocarbons. In general, it is desirable that the absorbents have a very high boiling point and at the same time very high solubility for isobutane and/or isobutene and very low solubility for the other residual gas components.

Examples of useful absorbents include aliphatic hydrocarbons, for example $C_8$–$C_{20}$-alkanes or -alkenes, or aromatic hydrocarbons, for example middle oil fractions from paraffin distillation, or ethers having bulky groups on the oxygen atom, or mixtures thereof, to which a polar solvent, for example the 1,2-dimethyl phthalate disclosed in DE-A 4308087. Further suitable absorbents include esters of benzoic acid and phthalic acid with straight-chain alkanols containing from 1 to 8 carbon atoms such as n-butyl benzoate, methyl benzoate, ethyl benzoate, dimethyl phthalate and diethyl phthalate, and also heat carrier oils such as diphenyl or diphenyl ether and mixtures of diphenyl and diphenyl:ether or chlorine derivatives thereof and triarylalkenes, for example 4-methyl-4'-bienzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A useful absorbent is also a solvent mixture of diphenyl and diphenyl ether, preferably in the azeotropic composition, in particular of about 25% by weight of diphenyl (biphenyl) and about 75% by weight of diphenyl ether, for example the commercially obtainable Diphenyl [sic]. Frequently, this solvent, mixture comprises a solvent such as dimethyl phthalate in an amount of from 0.1 to 25% by weight, based on the entire solvent mixture. Particularly useful absorbents also include octanes, nonanes, decanes, undecanes, dodecanes, tridecanes, tetradecanes, pentadecanes, hexadecanes, heptadecanes and octadecanes, and tetradecanes in particular have proven particularly useful. It is advantageous when the absorbent used on the one hand attains the abovementioned boiling point and on the other hand at the same time does not have too high a molecular weight. Advantageously, the molecular weight of the absorbent is $\leq 300$ g/mol. The paraffin oils having from 8 to 10 carbon atoms described in DE-A 3313573 are likewise suitable. Examples of useful trade products include the products sold by Haltermann including Halpasols®i, for example Halpasol 250/340i and Halpasol 250/275i, and also printing ink distillates sold as PKWF and Printosol.

The performance of the absorption is subject to no particular restrictions. All processes and conditions familiar to those skilled in the art may be used. Preference is given to contacting the gas mixture with the absorbent at a pressure of from 1 to 50 bar, preferably from 2 to 20 bar, more preferably from 5 to 10 bar, and a temperature of from 0 to 100° C., in particular from 30 to 50° C. The absorption may be carried out in absorption columns, for example tray columns having bubble cap and/or sieve trays, columns having structured packings or randomly packed columns, in trickle and spray towers, graphite block absorbers, surface absorbers such as thick film and thin film absorbers and also plate scrubbers, cross-spray scrubbers and rotary scrubbers.

It may also be advantageous to carry out the absorption in a bubble column with or without internals.

The isobutare and/or isobutene may be removed from the absorbate by stripping, depressurization-evaporation (flashing) and/or distillation (rectification).

Gases suitable for stripping are in particular those which may be recycled into reaction zone A together with the isobutane and isobutene.

Such gases include nitrogen, air, oxygen, oxygen/nitrogen mixtures, isobutane and steam. When air or oxygen/nitrogen mixtures are used where the oxygen content is above 10% by volume, it may be sensible to add a gas which reduces the explosion range before or during the stripping process. Particularly suitable gases for this purpose have a heat capacity of $\geq 29$ J/mol-K (based on 25° C. and 1 atm). For example, isobutane may also be used as such a gas.

The isobutane and/or isobutene may also be removed from the absorbate by a distillation. In order to minimize absorbent losses, both the gas phase resulting from the stripping and a rising gas phase resulting from distillation may be scrubbed in countercurrent using water. The scrubbing water used may be condensed steam contained in the residual gas.

Otherwise, the procedure may bepas described in WO-0196271 using the example of propane/propene.

Further possible methods of removing isobutane and/or isobutene from the residual, gas are adsorption, rectification and partial condensation. Preference is given to carrying out a fractional pressure distillation at low temperatures. The pressure to be applied may be, for example, from 10 to 100 bar. Useful rectification columns include randomly packed columns, tray columns or columns having structured packing. Useful tray columns include those having dual-flow trays, bubble cap trays or valve trays. The reflux ratio may be, for example, from 1 to 10. Examples of other possible separating methods include pressure extraction, pressure swing adsorption, pressure scrubbing, partial condensation and pressure extraction [sic]. For the purposes of a fractional distillation, the separating line may, for example, be defined in such a manner that substantially all of those components whose boiling point is lower than the boiling point of isobutene are removed at the top of the rectification column. These components will primarily be the carbon oxides CO and $CO_2$ and also unconverted oxygen and $N_2$ and optionally also $H_2$. Steam may be recycled together with isobutane and isobutene into reaction zone A.

A more comprehensive description of the above-outlined removal of methacrylic acid and methacrolein from a product gas mixture such as product gas mixture C can be found in EP-B 297445.

However, it will be appreciated that the separating processes of U.S. Pat. No. 49,259,81 and U.S. Pat. No. 4,554,054 may also be used for this purpose.

It is common to all these processes that a residual gas comprising unconverted isobutane remains after the methacrylic acid removal.

This gas may also be recycled as such into reaction zone A. In order to avoid accumulation of gases such as nitrogen or $CO_2$ over the course of time in such a case, a portion of the residual gas may be bled off and, for example, combusted for the purposes of energy recovery. For the purposes of the present invention, it is possible to recycle no residual gas in reaction zone A and to combust the entire residual gas for the purposes of energy generation.

It will be appreciated that the process according to the invention may also be carried out by recycling only a portion of the residual gas unchanged into reaction zone A and removing isobutane and isobutene in the mixture only from the remaining portion and likewise recycling them into reaction zone A and/or into reaction zone B. In the latter case, the remaining portion of the residual gas is advantageously combined with the product gas mixture A.

It is also possible to utilize removed isobutane and/or isobutene for purposes other than recycling into reaction zone A (for example the preparation of isobutanol).

If the gas containing isobutane and isobutene to be recycled into reaction zone A still contains carbon monoxide, this may be catalytically selectively combusted to $CO_2$ before (or after) entry into reaction zone A. The heat of reaction released may be used to heat to the dehydrogenation temperature.

Catalytic postcombustion of CO contained in the residual gas to $CO_2$ may also be recommendable when removal of the carbon oxides from the residual gas is sought before it is recycled into reaction zone A (or another zone), because $CO_2$ can be comparatively easily removed (for example by scrubbing with a basic liquid).

When dehydrogenation catalysts are used which are sensitive toward oxygen or oxygen-containing compounds, these oxygenates will be removed from the residual gas before recycling of the residual gas into reaction zone A. This is unnecessary for the catalysts particularly recommended for the catalytic dehydrogenation in this document.

The advantage according to the invention of reduced isobutyraldehyde and isobutyric acid by-production is substantially independent of the multimetal oxide catalysts used in reaction zones B and C. Preference is given to using those multimetal oxide catalysts which are explicitly mentioned in this document. This advantage is also substantially independent of whether the volume-specific catalyst activity in reaction zones B and C is kept constant or increases or decreases along the reaction coordinate.

However, immediate use of the methacrolein-obtaining product gas mixture B to charge a reaction zone C is not the preferred variant according to the invention. In depth investigations have shown that this can be attributed to components other than methacrolein contained in the product gas mixture B reducing the selectivity of methacrylic acid formation in a downstream reaction zone C by having a negative influence on the catalyst performance, in particular with regard to long-term behavior. Immediate use of the methacrolein-containing product gas mixture B to charge a reaction zone C is not to be recommended when the conversion of isobutene in reaction zone B is less than 95 mol % or less than 98 mol % (frequently, the conversion of isobutene in the reaction zone B is from 60 to 95 mol %).

In other words, an advantageous procedure according to the invention is to remove at least a portion which normally comprises isobutane and isobutene, preferably at least 80 mol %, more preferably at least 90 mol % and most preferably at least 95 mol % (the molar basis is the sum of the molar amounts of individual components contained in the product gas mixture B; the removal does not have to be homogeneous over the different components; rather, it may, for example, capture individual components quantitatively and others only partially; only the sum has to achieve the percentage mentioned), of those components which boil at a lower temperature than methacrolein at atmospheric pressure before using the product gas mixture B to charge a reaction zone C or a reaction zone for preparing methacrylic esters such as methyl methacrylate. According to the invention, it is also recommended to remove the methacrolein substantially as such from the product gas mixture B and then to use it to charge a reaction zone C or for another further use such as the preparation of alkyl esters of methacrylic acid, for example the preparation of methyl methacrylate. For the abovementioned application purposes, the methacrolein will also optionally be removed substantially with any steam contained in the product gas mixture B.

The abovementioned removals may be carried out using known methods. Reference is hereby made to DE-A 3313573, DE-A 2400260, GB-A 1199432 and U.S. Pat. No. 4,234,519. For example, the product gas mixture may be subjected to a multistage fractional distillation, preferably under pressure. In the first stage, methacrolein and components having higher boiling points than methacrolein are removed in the liquid phase. This liquid may subsequently either be used as such to charge a reaction zone C or for esterification purposes or the methacrolein contained in it may first be removed pure overhead in a further fractional distillation stage. The isobutane and isobutene present may be removed via the liquid phase in a further fractional distillation stage from the components which are distilled overhead in the first fractional distillation stage, have lower boiling points than methacrolein and comprise isobutene and isobutane, and be recycled into reaction zone A. The gas mixture distilled overhead may, for example, be disposed of by incineration or, if required, be used as a diluent gas in reaction zones A, B and/or C. When only a limited sharpness is sufficient in the abovementioned separating steps, fractionations may also be replaced by simple condensations.

The desired removal can also be achieved, for example, by cooling the product gas mixture B and thus condensing out aqueous methacrolein. To completely remove the methacrolein from the remaining gas phase, the latter will be washed with a recirculating water stream. The resulting aqueous methacrolein solutions may then be stripped off to obtain methacrolein-containing steam which may be used for esterification purposes or to charge a reaction zone C.

In practice, the procedure will be to cool the product gas mixture B by direct cooling with water or with an aqueous methacrolein solution (each of which is polymerization-inhibited using hydroquinone or its methyl ether) (by spraying the water or the aqueous methacrolein solution into the product gas mixture B and subsequently conducting in cocurrent). To remove any mist which forms the gas stream may subsequently be conducted through Venturi separators. The cooling liquid is, for example, circulated via a heat exchanger. It will be appreciated that the cooling may also be indirect. The cooled gas mixture is then conducted to an absorption apparatus (for example randomly packed column or tray column) in which the methacrolein (generally in countercurrent operation) is absorbed in a stream of recirculating water (for example at temperatures in the range from 15 to 20° C.).

The absorbate obtained is an aqueous methacrolein solution which may comprise, for example, up to 2 mol % or more methacrolein. In a stripper, the methacrolein may be stripped from water at reduced pressure and using heat and taken off as vapor stream (the water contained therein may, if required, be frozen and/or condensed off). The water which has been stripped off is, for example, recycled back into the methacrolein absorber for absorption purposes. The proportion of the water formed in the process (the steam contained in the product gas mixture B condensed and absorbed with the methacrolein in the absorption liquid) may either be disposed of (for example discharged to a sewer) and/or recycled as steam into reaction zone A.

The gas stream leaving the, methacrolein absorber comprises isobutene, isobutane, noble gases, carbon oxides, hydrogen, oxygen, nitrogen and other by-products such as ethane, propane or methane. It may either be recycled as such into reaction zone A (while bleeding off a portion to prevent by-product accumulation) or the products of value isobutane and isobutene contained therein can be removed by absorption in a nonpolar organic solvent (cf. the removal of isobutane and isobutene from residual gas already described in this document; all methods cited there may correspondingly be applied here).and subsequent desorption and recycled into reaction zone A. The unabsorbed gas components may in turn be disposed of and/or find use as diluent gases in reaction zones A, B and/or C.

Instead of recycling removed isobutane, isobutene or gases comprising these components into reaction zone A, they may also be utilized in another way. For example, they maybe combusted in a power station for the purpose of energy generation or used to prepare isobutanol.

It will be appreciated that another possible procedure is to recycle only a portion of the isobutane- and isobutene-containing gas which has been substantially freed of methacrolein as such into reaction zone A and to remove isobutane and isobutene in the mixture only from the remaining portion and likewise recycle them into reaction zone A and/or reaction zone B or to use them in another way.

It is here likewise the case that if the isobutane- and isobutene-containing gas to be recycled into reaction zone A still comprises CO, the CO may be combusted catalytically and selectively to $CO_2$ before (and/or after) its entry into reaction zone A. The heat of reaction released may in turn find use in heating to the dehydrogenation temperature.

Such a catalytic postcombustion of CO to $CO_2$ may also be recommendable when the intention is to remove the carbon oxides before recycling the gas stream into reaction zone A (or into another zone) because $CO_2$ can be comparatively easily removed (for example by scrubbing with a basic liquid; examples of useful liquids include aqueous carbonate or amine solutions or organic amines; since the presence of $CO_2$ does not interfere in any of the different reaction zones, carbon oxides will be allowed for economic reasons to accumulate in the recycle stream up to a concentration at which they can be conveniently and economically oxidized and/or removed).

When dehydrogenation catalysts are used which are sensitive toward oxygen or oxygen-containing compounds, these oxygenates will be removed from gas streams before they are recycled into reaction zone A. When the gas stream comprises hydrogen at the same time, it may be removed, for example, by the route of selective catalyzed combustion of $H_2$ to $H_2O$ using $O_2$. Equally, hydrogen may be removed from $H_2$-containing off gases which are to be disposed of, for example, by means of membrane processes and, if required, fed to reaction zone A.

However, the methacrolein may be removed from the product gas mixture B by other known methods, for example by extraction using a suitable organic solvent and subsequent rectificative workup or by adsorption [sic] and subsequent desorption.

It is essential to the invention that the methacrolein which has been partially or completely freed of secondary components as described will always contain less isobutyraldehyde or isobutyric acid than methacrolein obtained according to the process of the nearest prior art with equal separating effort.

Methacrolein which has been partially or completely freed of secondary components in this manner may then be used advantageously, for example, for preparing alkyl esters of methacrylic acid, in particular methyl methacrylate. To this end, the methacrolein will be reacted directly, with the appropriate alcohol, for example methanol, in the presence of oxygen and suitable catalysts. To this end, the prior art processes may be used, as described, for example, in DE-A 3018071, U.S. Pat. No. 6,107,515 or GB-A 2070601. Customarily, the reaction is effected in the liquid phase using catalysts comprising noble metals such as palladium.

However, it may also be used in a manner known per se for selective gas phase catalytic oxidative preparation of methacrylic acid.

Catalysts which may be used include the multimetal oxide catalysts already recommended for reaction zone B. Otherwise, the gas phase oxidation of methacrolein to methacrylic acid may be carried out as recommended in the prior art (cf., for example, U.S. Pat. No. 5,166,119, U.S. Pat. No. 5,153,162, U.S. Pat. No. 4,954,650, U.S. Pat. No. 4,558,028 and DE-A 19 815 279). The methacrylic acid may be removed from the product gas mixture as already described for reaction zone C (cf. DE-A 19 836 477).

The reactors described as suitable for reaction zone C may also be used here. Owing to the substantial heat of reaction, preference is given to diluting the reaction partners methacrolein and $O_2$ with inert gas such as $N_2$, $CO_2$, saturated hydrocarbons (for example isobutane) and/or with steam.

The oxygen source used may be pure molecular oxygen or molecular oxygen diluted with inert gases, for example (preferably) air.

In general, operation is effected at a molar methacrolein oxygen:steam inert gas ratio of from 2 to 6:(from 2 to 20):(from 5 to 30):(from 0 to 6), more preferably from 3 to 5:(from 7 to 12):(from 15 to 25):(from 0 to 4). The gas phase oxidation itself, like reaction zone B, may be realized either in fluidized bed reactors or else in fixed bed reactors. Preference is given to the latter. The reaction temperature is customarily in the range from 230 to 350° C. and the reaction pressure in the range from 0.5 to 3 bar and the total space velocity is preferably from 1000 to 4000 l at STP/1·h. The methacrolein conversion based (as always in this document) on single reactor pass is customarily from 60 to 90 mol %. The removal of the methacrylic acid from the product gas mixture may be carried out as already described with regard to reaction zone C. In other words, the product gas mixture may be scrubbed with water after direct and/or indirect cooling at temperatures of from 40° C. to 80° C. to obtain an aqueous methacrylic acid solution from which the methacrylic may be removed, for example, by extraction with an organic solvent and removed from it by rectification.

When required, the residual gas leaving the absorber may be used as an inert diluent gas in the reaction zones A, B and/or C and/or be disposed of, for example, by combustion.

When isobutane is one of the diluent gases used, the isobutane-containing residual gas is advantageously recycled into reaction zone A either as such or after absorption and desorption in the nonpolar organic solvents already recommended.

It is quite generally the case that when gases recycled into the reaction zone A comprise $O_2$, this oxygen may be used in the reaction zone A to selectively combust combustible substances such as hydrocarbons, coke, CO or preferably $H_2$ in reaction zone A, in order to thus generate the heat of dehydrogenation required in reaction zone A. Advantageously, the methacrolein oxidation will be carried out with an appropriate oxygen excess so that the abovementioned residual gas recycled into reaction zone A has a sufficient amount of oxygen for this-purpose.

EXAMPLES

1. Preparation of a Dehydrogenation Reactor

A solution of 11.993 g of $SnCl_2.2H_2O$ and 7.886 g of $H_2PtCl_6.6H_2O$ in 600 ml of ethanol are poured over 1000 g of a spalled $ZrO_2.SiO_2$ mixed oxide.

The mixed oxide has a $ZrO_2/SiO_2$ weight ratio of 95:5. The mixed oxide is manufactured by Norton (USA).

The mixed oxide has the following specification:

Type AXZ 311070306, Lot No. 2000160042, sieve fraction from 1.6 to 2 mm, BET surface area: 86 $m^2$/g, pore volume: 0.28 ml/g (mercury porosimetry measurement).

The supernatant ethanol is taken off on a Rotavapor by rotating in a water jet pump vacuum (20 mbar) at a waterbath temperature of 40° C. Drying is then effected at 100° C. for 15 h and then calcining at 560° C. over 3 h, both under stationary air. A solution of 7.71 g of $CsNO_3$, 13.559 g of $KNO_3$ and 98.33 g of $La(NO3)_3.6H_2O$ in 2500 ml of $H_2O$ is then poured over the dry solids. The supernatant water is taken off on a Rotavapor by rotating in a water jet pump vacuum (20 mbar) at a water temperature of 85° C. Drying is then effected at 100° C. for 15. h and then calcining at 560° C. over 3 h, both under stationary air.

The resulting catalyst precursor has a composition of $Pt_{0.3}Sn_{0.6}Cs_{0.5}K_{0.5}La_{3.0}$ (stoichiometric coefficients represent weight ratios) on $(ZrO_2)_{95}$ $(SiO_2)_5$ (stoichiometric coefficients represent weight ratios).

20 ml of the catalyst precursor obtained are used to charge a vertical tube reactor (reactor length: 800 nm [sic]; wall thickness: 2 mm, internal diameter: 20 mm; reactor material: internally alonized (i.e. aluminum oxide-coated) steel tube; heating: electrical (furnace from HTM Reetz, LOBA 1100-28-650-2) to a longitudinal average length of 650 mm; length of the catalyst bed: 75 mm; position of the catalyst bed: at the longitudinal midpoint of the tubular reactor; filling of the remaining reactor volume above and below with steatite spheres (inert material) of 4–5 mm diameter, supported from below on a catalyst base).

The reaction tube is then charged at an external wall temperature along the heating zone of 500° C. under closed loop control (based on a tube flowed through by an identical inert gas stream) with 9.3 l/h (STP) of hydrogen over 30 min. The hydrogen is then replaced at constant wall temperature firstly by a 23.6 l/h (STP) stream of 80% by volume of nitrogen and 20% by volume of air over 30 min and then by an identical stream of pure air over 30 min. While maintaining the wall temperature, purging is then effected using an identical stream of N₂ over 15 min and finally reduction using 9.3 l/h (STP) of hydrogen again over 30 min. The activation of the catalyst precursor is then complete. This results in a dehydrogenation reactor charged with dehydrogenation catalyst A (reaction zone A reactor).

2. Preparation of a Reaction Zone B Reactor a) Preparation of a Starting Composition B1

To prepare the starting catalyst B1, 2000 g of $(NH_4)_6Mo_7O_{24}\cdot 4H_2O$ are dissolved in portions in 5.4 l of water at 60° C. and admixed with stirring with 9.2 g of a 47.5% by weight aqueous KOH solution at 20° C. and then with 387.8 g of a 47.5% by weight aqueous $CsNO_3$ solution at 20° C. while maintaining the temperature at 60° C. (starting solution 1). A starting solution 2 is prepared by stirring 1123.6 g of an aqueous iron nitrate solution (13.8% by weight of Fe) into 2449.5 g of an aqueous cobalt nitrate solution (12.5% by weight of Co) at 60° C. while maintaining the temperature at 60° C.

Within a period of 30 min, the starting solution 2 at 60° C. is stirred into the starting solution 1 at 60° C. 15 min after stirring has ended, 157.0 g of silica sol (density: 1.39 g/ml; pH=8.8; alkali metal content: ≦0.5% by weight, 50.0% by weight of $SiO_2$; manufacturer: Dupont; Ludox®TM) are stirred into the aqueous suspension obtained (at 60° C.). The aqueous mixture is then stirred for a further 15 minutes. The aqueous suspension is then spray-dried (exit temperature: 110° C., spray dryer from Niro DK; model: Niro A/S Atomizer Mobile Minor, centrifugal atomizer from Niro, DK), to obtain a spray powder of particle size from 20 μm to 25 μm having a glow loss (3 h at 600° C. under air) of about 30% by weight. This spray powder forms the starting composition B1.

b) Preparation of a Starting Composition B2

1715.6 g of tungstic acid (72.94% by weight of W) are added in portions to 6344.6 g of an aqueous tungsten nitrate solution in nitric acid (free nitric acid: 4% by weight, density: 1.24 mg/l; 11.2% by weight of bismuth) at 20° C. with stirring. This gives an aqueous suspension which is stirred at 20° C. for a further 2 h. This is then dried by spray drying (exit temperature: 110° C., manufacturer: Niro DK; model: Niro A/S Atomizer Mobile Minor, centrifugal atomizer from Niro, DK). In this manner, a spray powder of particle size from 20 μm to 25 μm is obtained which has a glow loss (3 h at 600° C. under air) of about 12% by weight. After addition of 37 g of water, 400 g of this powder are kneaded using a Werner & Pfleiderer LUK 075 kneader (kneader has two sigma blades operating in contrarotation) for 30 min. After the kneading, the kneaded material is roughly divided and dried for 2 h in a drying cabinet (Binder, DE, type: FD 53) at 120° C. The entire amount of the dried material is calcined in a muffle furnace from Nabertherm, capacity about 120 l, at 800° C. over 2 h under an air stream of 1000 l/h (STP). The air stream is at about 20° C. when it is passed into the muffle furnace. Heating to the calcination temperature is effected linearly from 25° C. within 8 h.

The calcined material is then milled to a number average particle size (narrow distribution, longest dimension) of about 5 μm and mixed with 1% by weight (based on the $SiO_2$-free composition) of finely divided $SiO_2$ (bulk density: 150 g/l; number average particle size: 10 μm (longest dimension, narrow distribution); BET surface area: 100 m²/g).

This mixture forms the starting composition B2 c) Catalyst Preparation 1096 g of starting composition B1 and 200 g of starting composition B2 are mixed homogeneously with the addition of (based on the overall composition of B1 and B2 used) 1.5% by weight of finely divided graphite (according to sieve analysis min. 50% by weight<24 μm; 24 μm<max. 10% by weight<48 μm; 5% by weight>48 μm; BET surface area: 10 m²/g) as a tableting aid. This gives a mixture which has the following molar elemental stoichiometry (after calcination):

$[Bi_2W_2O_9\cdot 2WO_3]_{0.5}$
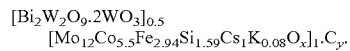
$[Mo_{12}Co_{5.5}Fe_{2.94}Si_{1.59}Cs_1K_{0.08}O_x]_1\cdot C_y$.

Circular solid tablets of diameter 16 mm and height 3 mm are pressed from the mixture. The pressing pressure is 9 bar. The tablets are comminuted and sieved through a sieve (0.8 mm mesh size). The material which passes through the sieve, after addition of 2% by weight of graphite (based on the weight of the material which passes through the sieve) is tableted in a tablet pressing machine (Kilian S100, pressing force: 15–20 N) into cylindrical rings of geometry 5 mm (external diameter)×3 mm (height)×2 mm (hole diameter).

150 g of these rings are calcined in a forced-air oven (Nabertherm, about 80 l capacity) as follows:

a) linear heating is effected from room temperature to 180° C. within 2 h and this temperature is maintained for 1 h;
b) linear heating is then effected from 180° C. to 210° C. within 1 h and this temperature is maintained for 1 h;
c) linear heating is then effected from 210° C. to 250° C. within 1 h and this temperature is maintained for 1 h;
d) linear heating is then effected from 250° C. to 450° C. within 1.5 h and this temperature is maintained for 10 h;
e) finally, the oven is left to cool by itself to room temperature (about 25° C.).

During the entire calcination, 150 l/h (STP) of air are passed through the oven.

The end product forms the multimetal oxide catalyst B to be used in reaction zone B.

d) Charging of the Reaction Zone B Reactor

A vertical reactor tube (tube length: 1500 mm; wall thickness: 2.5 mm; internal diameter: 15 nun; reactor material: V2A steel; in a furnace from HTM Reetz at a longitudinal midpoint length of 1300 mm, the remaining tube length at the tube entrance and the remaining tube length at the tube exit are heated with electrical heating bands) is charged with 100 g of catalyst B. The length of the catalyst bed is 650 mm. The position of the catalyst bed in the reaction tube is at the longitudinal midpoint. The remaining reaction tube volume above and below is filled with steatite spheres (inert material; 2–3 mm diameter), and the entire reaction tube charge is supported from below on a catalyst base of 10 cm height.

3. Preparation of a Reaction Zone C Reactor a) Preparation of a Starting Composition C1

4620 g of $(NH_4)_6Mo_7O_{24}\cdot 4H_2O$ and 153.2 g of $NH_4VO_3$ are dissolved at 60° C. with constant stirring in 5 l of water preheated to 60° C. While maintaining the temperature at 60° C., 421.7 g of a 76% by weight aqueous $H_3PO_4$ solution are added dropwise to this solution within 1 min with stirring. First 10.9 g of diammonium sulfate and then 317.8 g of pulverulent $Sb_2O_3$ (senarmontite) are then incorporated. The resulting mixture is then heated to 90° C. within 30 min (mixture 1). In parallel, 424.9 g of $CsNO_3$ are dissolved at 90° C. in 850 ml of water preheated to 90° C. to give a solution 1. While maintaining the temperature at 90° C., 446.5 g of an aqueous copper nitrate solution (15.5% by weight of copper) at 90° C. are added dropwise to mixture 1 within 4 min with continuous stirring. Spray-drying is then effected at an exit temperature of 110° C. (Niro DK, model: Niro A/S Atomizer Mobile Minor, centrifugal atomizer from Niro, DK). A spray powder of particle size from 20 to 30 μm is obtained which forms the starting composition C1 and has the following molar elemental stoichiometry (after calcination):

$Mo_{12}P_{1.5}V_{0.6}Cs_1Cu_{0.5}Sb_1S_{0.04}O_x$.

b) Preparation of a Starting Composition C2

880 g of pulverulent $Sb_2O_3$ (senarmontite) having an Sb content of 83% by weight are suspended with stirring in 4 l of water at 20° C. While maintaining the temperature at 20° C., a solution of 670.5 g of $Cu(NO_3)_2.2H_2O$ in 4 l of water is stirred into the suspension. This gives an aqueous suspension which is stirred at 80° C. for a further 2 h and is then spray-dried (exit temperature: 110° C., Niro DK, model: Niro A/S Atomizer Mobile Minor, centrifugal atomizer from Niro, DK). The spray powder has a particle size of 20–30 μm. 700 g of the spray powder are thermally treated in a cylindrical rotary furnace (length of the calcination chamber 0.50 m; internal diameter: 12.5 cm) while passing through 200 l/h (STP) of air as follows: within 1 h, linear heating is effected to 150° C. Linear heating is then effected to 200° C. within 4 h. Afterwards, linear heating is effected to 300° C. within 2 h and then to 400° C. within 2 h. Finally, linear heating is effected to 900° C. within 48 h.

After cooling to room temperature, a powder is obtained which has a specific BET surface area of 0.3 m²/g. This powder forms the starting composition C2 and substantially has the diffraction reflections of $CuSb_2O_6$ (comparative spectrum 17-0284 from the JCPDS-ICDD index). The starting composition C2 has the following molar elemental stoichiometry:

$CuSb_2O_6$.

c) Catalyst Preparation

The amounts of the starting composition C1 and the starting composition C2 corresponding to the mixing stoichiometry (after calcination) $(Mo_{12}P_{1.5}V_{0.6}Cs_1Cu_{0.5}Sb_2S_{0.04}O_x)_1.(Cu_1Sb_2O_6)_{0.5}$ are intimately mixed. 2% by weight of finely divided graphite (according to sieve analysis, min. 50% by weight <24 μm; 24 μm<max. 10% by weight<48 μm; 5% by weight>48 μm; BET surface: 10 m²/g) are then admixed into 500 g of the abovementioned mixture as a tableting aid.

A tablet pressing machine (Kilian S 100) is used without the addition of further additives to shape cylindrical rings of geometry 7 mm (external diameter)×7 mm (height)×3 mm (hole diameter) from the mixture.

500 g of the rings are then thermally treated in a forced-air oven (Nabertherm, capacity about 80 l) under a constant air stream (500 l/h (STP)·kg of solid) as follows: heating is effected at 4° C./min from 25° C. to 270° C. while maintaining the intermediate temperatures of 180° C. and 220° C. and the end temperature of 270° C. for 30 minutes each. Finally, the temperature is increased at a rate of 2° C./min to 370° C. and this temperature is maintained, over 6 h.

Cooling is then effected to room temperature and the hollow cylinders are processed to spall having a longest dimension of 1.6–3 mm. This spall forms a multimetal catalyst C to be used in reaction zone C.

d) Charging of the Reaction Zone C Reactor

A vertical reactor tube (tube length: 1800 mm; wall thickness: 1 mm; internal diameter: 8 mm; reactor material: V2A steel; in a furnace from. HTM Reetz at a longitudinal midpoint length of 1600 mm) is charged with 75 g of the multimetal oxide catalyst C. The length of the catalyst bed is 1000 mm. The position of the catalyst bed in the reaction tube is at the longitudinal midpoint. Above and below, the remaining reaction tube volume is filled with steatite spheres (inert material; diameter: 2–3 mm), and the entire reaction tube charge is supported from below on a catalyst base of height 10 cm. The remaining tube length at,the tube entrance and the remaining tube length at the tube exit is heated with electrical heating bands.

4. Performance of the Process According to the Invention

A) The reaction zone A reactor from 1. at an external wall temperature along the heating zone of 500° C. under closed loop control (based on a tube flowed through by an identical inert gas stream) is charged with a reaction gas mixture of 20 l/h (STP) of isobutane, 10 l/h (STP) of air and 8 g/h of steam.

The isobutane is metered in using a mass flow regulator from Brooks, while the water is first metered into an evaporator using an HPLC pump 420 from Kontron, evaporated in it and then mixed with the isobutane and the air. During the charging, the temperature of the charging gas mixture is 150° C. The starting pressure in the tube reactor is set to 1.5 bar by means of a pressure regulator from REKO disposed at the reactor exit.

Downstream of the pressure regulator, the product gas mixture A is depressurized to atmospheric pressure and cooled, and the steam contained therein condenses out. The gas remaining is analyzed by means of GC (HP 6890 with Chem.-Station, detectors: FID; TCD, separating columns: $Al_2O_3$/KCl (Chrompack), Carboxen 1010 (Supelco)). In a corresponding manner, the charging gas mixture is also analyzed.

After an operating time of three weeks, the following. analytical results are obtained:

|  | Charging gas mixture (% by volume) | Product gas mixture A (% by volume) |
|---|---|---|
| isobutane | 50 | 33 |
| isobutene | — | 10 |
| Nitrogen | 20 | 17.5 |
| Steam | 25 | 26 |
| Oxygen | 5 | — |
| CO | — | <0.1 |
| $CO_2$ | — | 2.5 |
| $H_2$ | — | 11 |
| Propene | — | <0.1 |
| Propane | — | <0.1 |
| Ethene | — | <0.1 |
| Ethane | — | <0.1 |

These values correspond to an isobutane conversion based on a single pass of 25 mol % and a selectivity of isobutene formation of 90 mol %.

The portion of the reaction zone B reactor from 2. in the oven is maintained by closed loop control at an external wall temperature (based on a tube flowed through by an identical inert gas stream) at which the isobutene conversion at a single pass of the reaction mixture is 92 mol %. The heating band at the reaction tube entrance (where the catalyst base is disposed) is likewise set to this temperature and the heating band at the reaction tube exit is set to a temperature 50° C. lower.

The charge consists of a mixture of 45 l/h (STP) of air (temp.=22° C.) and the 46 l/h (STP) of the product gas mixture A (temp.=500° C.). The air is metered in by means of a mass flow regulator from Brooks. The temperature of the charging gas mixture is increased to the reactor external wall temperature. The starting pressure in the reactor is set to 1.3 bar by means of a pressure regulator disposed at the reactor exit.

Downstream of the pressure regulator, the product gas mixture B (temperature=300° C.) is depressurized and analyzed by means of GC (HP 6890 with Chem.-Station, detectors: TCD, FID, separating columns: Poraplot Q (Chrompack), Carboxen 1010 (Supelco)). In an identical manner, the charging gas mixture is also analyzed.

After an operating time of 3 weeks, the following results are obtained:

|  | Charging gas mixture (% by volume) | Product gas mixture B (% by volume) |
| --- | --- | --- |
| isobutane | 16.5 | 16.5 |
| isobutene | 5 | 0.40 |
| $H_2$ | 5.5 | 5.5 |
| $O_2$ | 10 | 2.5 |
| $N_2$ | 48 | 47.5 |
| $H_2O$ | 13 | 19.5 |
| Methacrolein | — | 3.8 |
| Methacrylic acid | — | 0.1 |

These values correspond to an isobutene conversion based on single pass of 92 mol % and a selectivity of methacrolein formation of 84 mol %.

The portion of the reaction C reactor in the furnace is maintained by closed loop control at an external wall temperature of 290° C. (based on a tube flowed through by an identical inert gas stream). The heating band at the reaction tube entrance (where the catalyst [lacuna] is disposed) is set to 290° C. and the heating band at the reaction tube exit is set to 200° C. The charging gas mixture consists of 40 l/h (STP) of air (20° C.), 25 l/h (STP) of nitrogen (20° C.) and the remainder of the product gas mixture B which remains after removing all components having lower boiling points than methacrolein. This remainder substantially comprises 18 l/h (STP) of steam, 3.5 l/h (STP) of methacrolein and 0.1 l/h (STP) of methacrylic acid. The air and the nitrogen are metered in by means of mass flow regulators from Brooks. The temperature of the charging gas mixture is increased to 290° C.

The pressure at the reaction tube exit is set to 1.3 bar using a pressure regulator disposed at the reactor exit. Downstream of the pressure regulator, the product gas mixture C (temperature: 200° C.) is depressurized and analyzed by means of GC (HP 6890 with Chem.-Station, detectors: TCD, FID, separating columns: Poraplot Q (Chrompack), Carboxen 1010 (Supelco)). In a corresponding manner, the charting gas mixture is also analyzed.

After an operating time of 3 weeks, the following results are obtained:

|  | Charging gas mixture (% by volume) | Product gas mixture C (% by volume) |
| --- | --- | --- |
| $N_2$ | 66 | 66 |
| $O_2$ | 9 | 6 |
| $H_2O$ | 21 | 21 |
| Methacrolein | 4 | 1.6 |
| Methacrylic acid | 0.1 | 2 |

These values correspond to a-methacrolein conversion based on single pass of 60 mol % and a selectivity of methacrylic acid formation of 83 mol %.

B) The performance of the process according to the invention from A) is repeated, except that no components are removed from the product gas mixture B. Rather, the product gas mixture B is used as such (92 l/h (STP)) in a mixture with 29 l/h (STP) of air as the charging gas for the reaction zone C reactor.

The methacrolein and oxygen gas flows on the catalyst charge in the reaction zone C reactor are accordingly, as in A), 3.5 l/h (STP) of methacrolein and 8.0 l/h (STP) of oxygen.

After an operating time of 3 weeks, the following results are obtained:

|  | Charging gas mixture (% by volume) | Product gas mixture C (% by volume) |
| --- | --- | --- |
| $N_2$ | 55.5 | 55 |
| $O_2$ | 6.5 | 4.5 |
| $H_2O$ | 14.5 | 15.5 |
| Methacrolein | 2.9 | 1.8 |
| Methacrylic acid | 0.10 | 0.9 |
| isobutane | 12.5 | 12 |
| isobutene | 0.3 | 0.1 |
| $H_2$ | 4 | 4 |

These values correspond to a methacrolein conversion based on single pass of 40 mol % and a selectivity of met,hacrylic acid formation of 75 mol %.

5. Comparative Example

A) The process according to the invention 4.A) is repeated. However, when the reaction zone B reactor is charged, 9 l/h. (STP) of pure oxygen are used instead of 45 l/h (STP) of air. The total isobutyraldehyde+isobutyric acid content,of,the product gas mixture B is perceptibly increased compared to the experimental procedure 4.A).

B) The process according to the invention 4.B) is repeated, except that the charging gas used for the reaction zone C reactor is not 29 l/h (STP) of air but 5.8 l/h (STP) of pure oxygen. The total isobutyraldehyde+isobutyric acid content of the product gas mixture C is perceptibly increased compared to the experimental procedure 4.B).

We claim:
1. A process for preparing methacrolein from isobutane comprising
A) subjecting isobutane in a reaction zone A to a partial heterogeneously catalyzed dehydrogenation in the gas phase to form a product gas mixture A which comprises isobutene and unconverted isobutane,

B) passing product gas mixture A into a reaction zone B and subjecting the isobutene in the reaction zone B to a heterogeneously catalyzed partial oxidation in the gas phase with molecular oxygen to form a product gas mixture B which comprises methacrolein, and C) optionally, further reacting the methacrolein in the product gas mixture B and optionally recycling isobutane in the product gas mixture B into reaction zone A, wherein the molecular oxygen is added to reaction zone B with molecular nitrogen in a molar ratio of molecular oxygen to molecular nitrogen of from 1:1 to 1:10.

2. The process as claimed in claim 1, wherein the molecular oxygen in reaction zone B comprises air.

3. The process as claimed in claim 1, wherein the methacrolein in the product gas mixture B is reacted to form methacrylic acid and reacting includes separating from the components contained in product gas mixture B and having at atmospheric pressure a lower boiling point than methacrolein, at least an isobutane- and isobutene-containing portion B1 to obtain a remaining product gas mixture portion B2 enriched in methacrolein and then charging a reaction zone with the portion B2 to form methacrylic acid by the heterogeneously catalyzed gas phase partial oxidation of methacrolein.

4. The process as claimed in claim 3, further comprising separating isobutane and isobutene from the isobutane- and isobutene-containing portion B1 by absorption in a nonpolar organic solvent, and the isobutane and isobutene are freed from the organic solvent by subsequent desorption, stripping or both desorption and stripping, and recycled into reaction zone A.

5. The process as claimed in claim 1, further comprising reacting the methacrolein in the product gas mixture B to form methyl methacrylate, wherein reacting includes separating from the components contained in the product gas mixture B and having at atmospheric pressure a boiling point lower than the boiling point of methacrolein, at least an isobutane- and isobutene-containing portion B1 to obtain a remaining product gas mixture portion B2 enriched in methacrolein and then charging a reaction zone with the portion B2 to react the methacrolein with methanol in the liquid phase in the presence of oxygen and a catalyst to form methyl methacrylate.

6. The process as claimed in claim 5, further comprising separating isobutane and isobutene from the isobutane- and isobutene-containing portion B1 by absorption in a nonpolar organic solvent, and the isobutane and isobutene are freed from the organic solvent by subsequent desorption, stripping or both desorption and stripping, and recycled into reaction zone A.

7. The process as claimed in claim 1, wherein the methacrolein in the product gas mixture B is reacted to form methacrylic acid by charging the methacrolein-containing product gas mixture B into a reaction zone in which the methacrolein is subjected to a heterogeneously catalyzed gas phase partial oxidation to form methacrylic acid.

8. The process as claimed in claim 1, comprising further reacting the methacrolein in the product gas mixture B to form methacrylic acid.

9. The process as claimed in claim 1, wherein the molar ratio of the amount of molecular nitrogen charged to reaction zone B to the amount of isobutene contained in product gas mixture A is $\leq 20:1$.

10. The process as claimed in claim 9, wherein said molar ratio of molecular nitrogen to isobutene is $\leq 12:1$.

11. The process as claimed in claim 1, wherein the molar ratio of the amount of molecular nitrogen charged to reaction zone B to the amount of isobutene contained in product gas mixture A is from 1:1 to 20:1.

12. The process as claimed in claim 11, wherein said molar ratio of molecular nitrogen to isobutane is from 2:1 to 16:1.

13. The process as claimed in claim 12, wherein said molar ratio of molecular nitrogen to isobutane is from 2:1 to 6:1.

14. The process as claimed in claim 1, wherein materials charged into reaction zone B are present in the following molar ratio:

isobutane:isobutene:$N_2$:$O_2$:$H_2O$:$H_2$:others=10–40:4–8:20–80:5–20:0–20:0–10:0–5.

15. The process as claimed in claim 14, wherein said molar ratio of materials is:
10–25:4–8:40–80:10–15:5–15:2–6:0.1–3.

* * * * *